US009669239B2

(12) United States Patent
Carpentier

(10) Patent No.: US 9,669,239 B2
(45) Date of Patent: Jun. 6, 2017

(54) DEVICE FOR TREATING THE SENSORY CAPACITY OF A PERSON AND METHOD OF TREATMENT WITH THE HELP OF SUCH A DEVICE

(75) Inventor: Alexandre Carpentier, Paris (FR)

(73) Assignee: UNIVERSITE PIERRE ET MARIE CURIE (PARIS 6), Paris (FR)

( * ) Notice: Subject to any disclaimer, the term of this patent is extended or adjusted under 35 U.S.C. 154(b) by 272 days.

(21) Appl. No.: 14/234,672

(22) PCT Filed: Jul. 24, 2012

(86) PCT No.: PCT/FR2012/051757
§ 371 (c)(1),
(2), (4) Date: Apr. 20, 2014

(87) PCT Pub. No.: WO2013/017778
PCT Pub. Date: Feb. 7, 2013

(65) Prior Publication Data
US 2014/0249454 A1 Sep. 4, 2014

Related U.S. Application Data

(60) Provisional application No. 61/512,087, filed on Jul. 27, 2011.

(30) Foreign Application Priority Data

Jul. 27, 2011 (FR) ...................... 11 56862

(51) Int. Cl.
A61H 1/00 (2006.01)
A61N 7/00 (2006.01)
(Continued)

(52) U.S. Cl.
CPC .............. A61N 7/00 (2013.01); A61B 8/0816 (2013.01); A61B 8/582 (2013.01); A61N 1/0531 (2013.01);
(Continued)

(58) Field of Classification Search
CPC .............................. A61N 7/00; A61H 23/0245
See application file for complete search history.

(56) References Cited

U.S. PATENT DOCUMENTS 4,982,434 A 1/1991 Lenhardt et al.
5,391,197 A 2/1995 Burdette et al.
(Continued)

FOREIGN PATENT DOCUMENTS

EP 0 701 840 3/1996
EP 1 262 160 12/2002
(Continued)

OTHER PUBLICATIONS

Carpentier et al., "Identification Du Gyrus . . . IRM Fonctionnelle", Neurochirurgie, 2002, 48, No. 2-3, 80-86.
(Continued)

Primary Examiner — Tse Chen
Assistant Examiner — Hien Nguyen
(74) Attorney, Agent, or Firm — Clark & Brody

(57) ABSTRACT

A system for treating at least one sensory capacity of a person with the help of a stimulation device comprises an electronic converter of a sensory signal into an electronic signal for controlling at least one transducer for emitting signals that are images of the sensory signal. The stimulation device for direct ultrasound stimulation of the sensory cortex of a brain comprises at least one support that is implantable in a skull and that includes at least one internal wall and at least one ultrasound transducer carried by the support. Means for emitting focused ultrasound waves through the internal wall of the support towards a determined zone of the sensory cortex of the patient's brain in order to generate modulation of the brain activity in the cortex are provided.
(Continued)

The ultrasound transducer is driven by the electronic converter to emit focused ultrasound signals that are images of the sensory signal.

17 Claims, 4 Drawing Sheets

(51) Int. Cl.
| | |
|---|---|
| *A61N 1/375* | (2006.01) |
| *A61N 1/05* | (2006.01) |
| *A61N 1/36* | (2006.01) |
| *A61B 8/08* | (2006.01) |
| *A61B 8/00* | (2006.01) |
| *H04R 25/00* | (2006.01) |

(52) U.S. Cl.
CPC ....... *A61N 1/0539* (2013.01); *A61N 1/36064* (2013.01); *A61N 1/3756* (2013.01); *A61N 2007/0026* (2013.01); *H04R 25/353* (2013.01); *H04R 2225/67* (2013.01)

(56) References Cited

U.S. PATENT DOCUMENTS

| | | |
|---|---|---|
| 5,429,582 A | 7/1995 | Williams |
| 5,524,624 A | 6/1996 | Tepper et al. |
| 6,248,126 B1 | 6/2001 | Lesser et al. |
| 6,319,241 B1 | 11/2001 | King et al. |
| 6,321,104 B1 | 11/2001 | Gielen et al. |
| 6,468,219 B1 | 10/2002 | Njemanze |
| 6,560,486 B1 | 5/2003 | Osorio et al. |
| 6,584,357 B1 | 6/2003 | Dawson |
| 6,666,833 B1 | 12/2003 | Friedman et al. |
| 6,862,479 B1 | 3/2005 | Whitehurst et al. |
| 7,302,298 B2 | 11/2007 | Lowry et al. |
| 7,421,297 B2 | 9/2008 | Giftakis et al. |
| 7,522,962 B1 | 4/2009 | Doron et al. |
| 7,717,853 B2 | 5/2010 | Nita |
| 7,949,401 B2 | 5/2011 | Fowler et al. |
| 8,644,940 B2 | 2/2014 | Forsell |
| 8,942,781 B2 | 1/2015 | Carpentier et al. |
| 8,977,361 B2 | 3/2015 | Carpentier et al. |
| 2001/0051819 A1* | 12/2001 | Fischell ............ A61N 1/3605 607/45 |
| 2002/0032393 A1 | 3/2002 | Talish et al. |
| 2002/0072741 A1 | 6/2002 | Sliwa, Jr. et al. |
| 2002/0111552 A1 | 8/2002 | Maor et al. |
| 2003/0225331 A1 | 12/2003 | Diederich et al. |
| 2003/0233136 A1 | 12/2003 | Williams et al. |
| 2004/0162507 A1 | 8/2004 | Govari |
| 2004/0267234 A1 | 12/2004 | Heart et al. |
| 2005/0015128 A1 | 1/2005 | Rezai et al. |
| 2005/0020945 A1 | 1/2005 | Tosaya et al. |
| 2005/0021117 A1 | 1/2005 | He et al. |
| 2005/0033171 A1* | 2/2005 | Stergiopoulos ........ A61B 5/031 600/437 |
| 2005/0240170 A1 | 10/2005 | Zhang et al. |
| 2005/0283203 A1 | 12/2005 | Flaherty et al. |
| 2006/0049957 A1 | 3/2006 | Surgenor et al. |
| 2006/0058708 A1 | 3/2006 | Heart et al. |
| 2006/0129204 A1 | 6/2006 | Pless et al. |
| 2006/0224060 A1 | 10/2006 | Garell et al. |
| 2007/0016040 A1 | 1/2007 | Nita |
| 2007/0038100 A1 | 2/2007 | Nita |
| 2007/0043268 A1 | 2/2007 | Russell |
| 2007/0067003 A1* | 3/2007 | Sanchez ............ A61N 1/36082 607/45 |
| 2007/0073135 A1 | 3/2007 | Lee et al. |
| 2007/0088345 A1 | 4/2007 | Larson et al. |
| 2007/0129652 A1 | 6/2007 | Nita |
| 2007/0179558 A1 | 8/2007 | Gliner et al. |
| 2007/0225773 A1 | 9/2007 | Shen et al. |
| 2007/0293908 A1 | 12/2007 | Cowan et al. |
| 2007/0299370 A1 | 12/2007 | Bystritsky |
| 2008/0004676 A1 | 1/2008 | Oskypka et al. |
| 2008/0039895 A1 | 2/2008 | Fowler et al. |
| 2008/0140149 A1 | 6/2008 | John et al. |
| 2008/0195160 A1 | 8/2008 | Wingeier et al. |
| 2008/0275526 A1 | 11/2008 | Lozano |
| 2008/0287837 A1 | 11/2008 | Makin et al. |
| 2009/0112278 A1 | 4/2009 | Wingeier et al. |
| 2009/0222067 A1 | 9/2009 | Toselli et al. |
| 2009/0248165 A1 | 10/2009 | Lin et al. |
| 2009/0254134 A1 | 10/2009 | Nikolov et al. |
| 2010/0002275 A9 | 1/2010 | Argoitia et al. |
| 2010/0036468 A1 | 2/2010 | Decre et al. |
| 2010/0041988 A1 | 2/2010 | Pijnenburg et al. |
| 2010/0137937 A1 | 6/2010 | John et al. |
| 2010/0145414 A1 | 6/2010 | Decre et al. |
| 2010/0217160 A1 | 8/2010 | Saguchi et al. |
| 2010/0222715 A1 | 9/2010 | Nita |
| 2010/0268088 A1 | 10/2010 | Prus et al. |
| 2011/0112394 A1 | 5/2011 | Mishelevich |
| 2011/0178441 A1* | 7/2011 | Tyler ................ A61N 7/00 601/2 |
| 2011/0178442 A1 | 7/2011 | Mishelevich |
| 2011/0213200 A1 | 9/2011 | Mishelevich |
| 2011/0245734 A1 | 10/2011 | Wagner et al. |
| 2011/0275963 A1* | 11/2011 | Wagner ............ A61N 1/0408 601/2 |
| 2012/0046531 A1 | 2/2012 | Hua |
| 2012/0065458 A1 | 3/2012 | Tol et al. |
| 2012/0078140 A1 | 3/2012 | Nita |
| 2012/0083719 A1 | 4/2012 | Mishelevich |
| 2012/0203079 A1 | 8/2012 | McLaughlin |
| 2013/0131754 A1 | 5/2013 | Sarvazyan |
| 2013/0178765 A1 | 7/2013 | Mishelevich et al. |
| 2013/0204316 A1 | 8/2013 | Carpentier et al. |
| 2013/0281890 A1 | 10/2013 | Mishelevich et al. |
| 2013/0324891 A1 | 12/2013 | Towe |
| 2014/0249454 A1 | 9/2014 | Carpentier |
| 2014/0288544 A1 | 9/2014 | Diederich et al. |
| 2014/0296646 A1 | 10/2014 | Wingeier et al. |
| 2014/0330123 A1 | 11/2014 | Manwaring et al. |
| 2015/0018727 A1 | 1/2015 | Diederich et al. |
| 2015/0141876 A1 | 5/2015 | Diederich et al. |
| 2015/0148710 A1 | 5/2015 | Towe et al. |
| 2015/0224345 A1 | 8/2015 | Warlick |
| 2015/0231417 A1 | 8/2015 | Metcalf et al. |
| 2015/0297176 A1 | 10/2015 | Rincker et al. |
| 2016/0000411 A1 | 1/2016 | Raju et al. |
| 2016/0001096 A1 | 1/2016 | Mishelevich |
| 2016/0016012 A1 | 1/2016 | Youn et al. |

FOREIGN PATENT DOCUMENTS

| | | |
|---|---|---|
| EP | 1 312 423 | 5/2003 |
| EP | 1 834 646 | 9/2007 |
| GB | 2 473 265 | 3/2011 |
| GR | 20070100349 | 1/2009 |
| JP | 2001-327495 | 11/2001 |
| JP | 2003-325616 | 11/2003 |
| JP | 2007-289715 | 11/2007 |
| WO | 96/39079 | 12/1996 |
| WO | 2004/052256 | 6/2004 |
| WO | 2005/065738 | 7/2005 |
| WO | 2006/042163 | 4/2006 |
| WO | 2009/132855 | 11/2009 |
| WO | 2010/009141 | 1/2010 |
| WO | 2011/029208 | 3/2011 |
| WO | 2013/048912 | 4/2013 |
| WO | 2013/177430 | 11/2013 |
| WO | 2015/075603 | 5/2015 |
| WO | 2015/079324 | 6/2015 |

OTHER PUBLICATIONS

Marat M. Rvachev, "Alternative model of propagation of spikes along neurons", Physics Department, Feb. 2, 2008, pp. 1-8.

(56) References Cited

OTHER PUBLICATIONS

Yusuf Tufail et al., "Transcranial Pulsed Ultrasound Stimulates Intact Brain Circuits", Neuron 66, 681-694, Jun. 10, 2010.

* cited by examiner

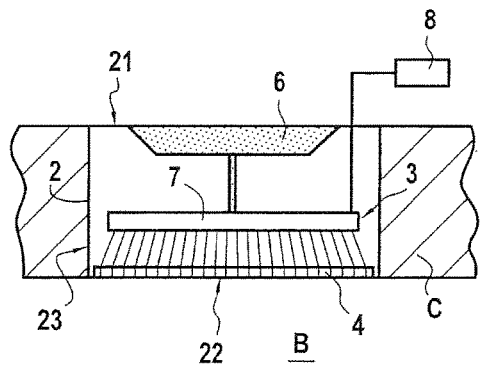
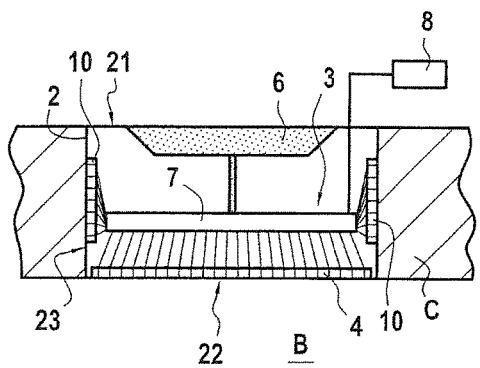
FIG.3  FIG.4
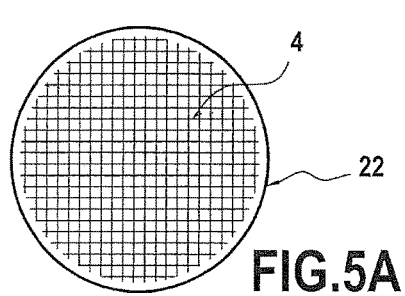
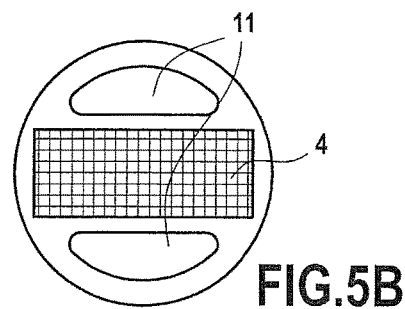
FIG.5A  FIG.5B
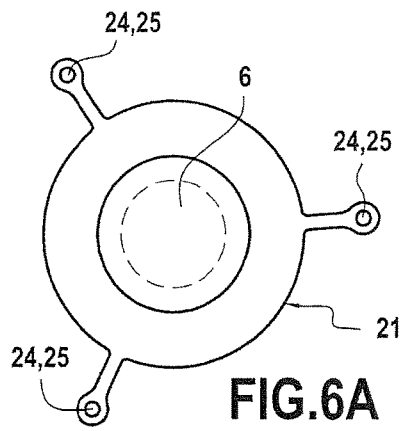
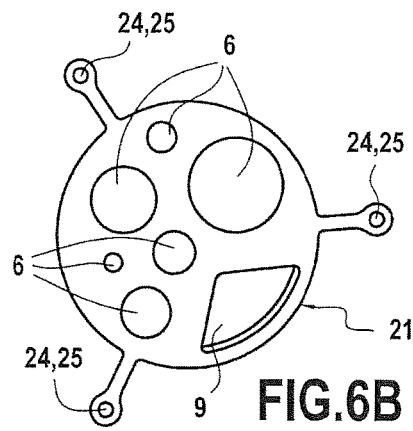
FIG.6A  FIG.6B

DEVICE FOR TREATING THE SENSORY CAPACITY OF A PERSON AND METHOD OF TREATMENT WITH THE HELP OF SUCH A DEVICE

FIELD OF THE INVENTION

The present invention relates to treating the sensory capacity of a person with the help of implantable devices, and it relates more particularly to treating in a broad sense any sensory capacities of a person, such as auditory, visual, olfactive, tactile, or even gustatory capacities.

BACKGROUND OF THE INVENTION

In a preferred application, the present invention relates to a device and a method for treating deafness that makes use of emitting ultrasound waves into the brain of a patient suffering from deafness or hearing difficulties.

In another preferred application, the present invention relates to a device and a method for treating vision that makes use of emitting ultrasound waves into the brain of a patient suffering from blindness or visual difficulties.

In the field of audition, deafness and hearing difficulties nowadays constitute a major medical problem insofar as these pathologies have considerable repercussions on the social lives of the patients concerned.

In general, the term "deafness" is used for patients suffering from a deep loss of hearing, generally a loss greater than 90 decibels (dB).

Three main categories of deafness are presently known.

Firstly there is so-called "conductive" deafness that involves pathologies of the middle ear.

There is also so-called "sensorineural" deafness that relates to diseases of the cochlea, situated in the inner ear or to malformations of the cochlea.

Finally, there is also so-called "neural" deafness which results from pathologies of the auditory nerve or the auditory cortices of the brain.

The physical and physiological mechanisms of hearing are particularly complex to understand.

The outer ear collects sounds and concentrates them inside the outer ear on the eardrum. The eardrum then transmits the perceived sounds by setting into vibration the ossicular chain contained in the cavity of the middle ear. The middle ear acts as a transmission amplifier with amplification being performed by the three small bones of the ossicular chain. The sound signal as amplified by the middle ear is then transmitted to the fluid-filled inner ear that is formed by the cochlea. The inner ear then transforms the signal into nervous excitation of the cochlear nerve. Each sound frequency corresponds to one or more specific activations of each of the fibers of the cochlear nerve.

The cochlear nerve is directed towards the eighth nucleus of the brain stem and the neurons relay and conduct the neural signal towards the primary auditory cortex known as Heschl's gyrus in Broadmann's area 41, and also to Broadmann's area 42 of the planar temporal gyrus (A. Carpentier et al., Neurochirurgie 2002; 48(2-3): pp. 80-86).

Thereafter, the neural signal is processed by secondary auditory areas (also known as "associative zones") of the brain before reaching the language area (Broadmann's area 22, also known as Wernicke's area).

In all cases of hearing difficulties and deafness, various solutions now exist to enable patients to be fitted, in particular with cochlear implants or indeed with brain-stem implants. For example, more than 188,000 patients throughout the world are receiving cochlear implants each year.

Nevertheless, such cochlear implants and brain-stem implants cannot restore hearing correctly for various reasons.

Firstly, those implants all rely on the concept of electrically stimulating neural tissue. Unfortunately, such stimulation is always associated with electrical diffusion phenomena in tissue and in particular in sensory tissue. Thus, any electrical stimulation of neural tissue ends up addressing a plurality of neural circuits without sufficient mastery over specificity.

Furthermore, the electrical stimulation devices that have been developed for cochlear implants or for brain-stem implants all have electrodes, and are thus highly invasive for the patients, thereby damaging or even completely destroying the weak natural residual auditory function.

Furthermore, electrical stimulation systems require implantation in or in contact with neural tissue, which also involves a risk of electrodes being wrongly or poorly positioned.

Finally, the electrical stimulation electrodes of cochlear implants and of brain-stem implants cannot comply accurately with the anatomic and functional organization of the neurons (somatotopy) insofar as the implantation zones are very dense in neurons, once more making it likely that several neural circuits will be activated simultaneously.

Consequently, patients having such implants can unfortunately perceive only very few different sounds, which does not enable them to follow a normal oral conversation at a usual sound level.

In order to solve some of those technical problems, research has been directed to developing electrical "grids" for positioning in direct contact with the surface of the temporal lobe of the brain. Nevertheless, many of the above-mentioned problems remain.

During electrical stimulation of such surface cortical grids, it is not possible to preserve somatotopy and diffusion of the peripheral cortex of the primary auditory cortex. Furthermore, since the primary auditory cortex is located more deeply than the surface of the temporal lobe on which the grid is applied, the resulting electrical excitation does not take place in the appropriate gyrus.

Other research teams have attempted to solve these problems by inserting brain electrodes. Nevertheless, that technique is particularly invasive and the movements of the electrodes, and of the grids, are incompatible with the physiological pulsatility of the brain inside the skull.

U.S. Pat. No. 4,982,434 discloses a system for treating deafness that is for fastening to a patient's skull. That system includes a microphone suitable for picking up ambient sounds. The microphone is connected via a converter to a transducer for applying vibrations to the skull of the patient. The vibrations applied to the skull are transmitted to the inner ear saccule that activates the cochlear nerve. Such a treatment system seeking to stimulate the auditory cortex indirectly via the inner ear is not suitable for correctly restoring hearing for the reasons mentioned above.

In the field of visual acuity, blindness and visual difficulties nowadays constitute a major medical problem insofar as these pathologies have considerable repercussions on the social lives of the patients concerned, who represent about 0.5% of the population. There are many potential causes for blindness: malformation; infection (toxoplasmosis); trauma; tumors (brain tumors); degenerative (age-related macular degeneration (ARMD)); vascular (diabetes, stroke). These pathologies may occur in the eyeball, and also anywhere along the nerve transmission path (optical nerve, chiasma, optic tracts, external geniculate bodies, optic radiation, visual cortex).

In the event of severe visual difficulties and blindnesses that cannot be improved medically or surgically, very artificial solutions for restoring vision have already been envisaged:

If the pathology involves the eyeball itself by damage to the cornea or the lens, the problem is not neurological but optical. Thus, artificial lenses are implanted to take the place of the cornea or of the natural lens.

If the pathology concerns neurological optical pathways, then there is at present no satisfactory system. Nevertheless, a large amount of research work has been carried out. It concerns either restoring the visual pathways by grafts or else developing artificial systems with detection by camera. An image picked up by a camera is processed and then used for activating defective natural visual pathways via an electrical interface. Those thus constitute devices for electrically stimulating neural tissue.

Electrical stimulation can be performed on the ganglion cells of the retina by installing plates of 16 to 40 electrodes.

The electrical stimulation may be performed directly on neural tissue (external geniculate ganglions, cerebral visual cortex) by putting plates into place having up to 242 electrodes, either on the surface of the visual cortex or implanted within the cortex.

At present, the most advanced appliances provide only rudimentary images in black and white that are still not sufficient for finding one's location in unknown surroundings. Implanting 242 electrodes in a brain can obtain tunnel vision only, being equivalent to rendering a photograph on a matrix of 15 pixels by 16 pixels. Several problems persist that explain this poor effectiveness:

The primary visual cortex is mainly deployed on the medial face of the brain, i.e. an internal face, where it is therefore difficult to put a deep electrode plate into position.

Plates with electrodes that penetrate into the brain provide the best presently-available visual rendering, but they are very traumatic for the cortex, and the quality of the connection deteriorates over time because of the appearance of insulating layers and because of the physiological pulsatile movements of the brain inside the skull.

Electrical stimulation is always associated with electrical diffusion phenomena within tissue, and in particular within sensory neural tissue. Thus, any electrical stimulation of neural tissue ends up addressing a plurality of neural circuits without specificity being sufficiently well controlled. It has been found that electrode density is presently limited not by manufacturing limits but by the effects of current and short circuits between electrodes that are too close together.

Thus, electrical stimulation electrodes cannot comply closely with the anatomical and functional organization of neurons (somatotopy) insofar as the implantation zones are very dense in neurons, once more giving rise to several neural circuits being activated simultaneously. Thus, such a treatment system seeking to stimulate the visual cortex indirectly is not suitable for correctly restoring vision for the reasons mentioned above.

In an entirely different field, it has nevertheless recently been shown that the use of pulsed focused ultrasounds can stimulate intact motor zones of the brain in non-invasive manner. Modulating neurons with ultrasound thus appears to be a technique that is favorable for designing non-invasive brain/machine interfaces for stimulating the brain.

By way of example, it has been shown in rats that ultrasound stimulation of the motor cortex leads to sufficient neural activity to trigger motor behavior of the subject (Y. Tufail, A. Matyushov, N. Baldwin, M L Tauchmann, J. Georges, A. Yoshihiro, S. I. Tillery, W J Tyler, "Transcranial pulsed ultrasound stimulates intact brain circuits" Neuron, Jun. 10, 2010; 66(5): pp. 681-694).

Such coupling of ultrasound techniques with neural physiology was mentioned for the first time in 2006 by Rvachev (M. M. Rvachev, "Alternative model of propagation of spikes along neurons", Physics 2006).

SUMMARY OF THE INVENTION

Based on those initial studies and for the purpose of solving problems recognized in present-day implants, an object of the present invention is to provide a novel device and a novel method for treating sensory capacity in patients.

The invention seeks more particularly to provide treatment means that are less traumatic and less invasive while being more accurate and more effective than presently-known methods and devices for treating sensory capacity of a patient.

An object of the invention is thus to provide a system for treating sensory capacity in a patient in order to remedy a deficiency, to assist the sensory capacity, or indeed to augment the sensory capacity.

In particular, the invention proposes a system for treating at least one sensory capacity of a person with the help of a stimulation device comprising an electronic converter of a sensory signal into an electronic signal for controlling at least one transducer for emitting signals that are images of the sensory signal. According to the invention, the stimulation device is a device for direct ultrasound stimulation of the sensory cortex of the patient's brain, and the ultrasound stimulation device comprises:

- at least one support that is implantable in the patient's skull and that includes at least one internal wall; and
- at least one ultrasound transducer carried by the support and including means for emitting focused ultrasound waves through the internal wall of the support towards a determined zone of the sensory cortex of the patient's brain in order to generate modulation of the brain activity in the cortex, the ultrasound transducer being driven by the electronic converter to emit focused ultrasound signals that are images of the sensory signal.

The treatment system of the invention also includes in combination one or more of the following additional characteristics:

- the ultrasound stimulation device including variable steering and focusing means for the ultrasound waves emitted towards the target zone of the sensory cortex;
- the steering and focusing means for the ultrasound waves comprising means for electronically scanning at least one zone of the sensory cortex for treatment with the emitted ultrasound waves;
- the bottom wall of the unit includes an external surface covered in a flexible material of varying thickness to provide a continuous contact interface with the brain or the dura mater and to facilitate propagation of ultrasound waves into the brain;
- the adjustment and control means comprise an external remote control for controlling and driving the ultrasound stimulation device wirelessly;
- the adjustment and control means comprise an external control device connectable to the ultrasound stimulation device;

the electrical power supply means comprise at least one rechargeable battery arranged in the unit or implanted under the skin of the patient's body;

a treatment system including electrodes on an external contact surface of the internal wall of the unit for monitoring the electrical activity of the brain and for preventing any epileptic event;

a treatment system including an emergency stop switch in the top wall of the support; and a treatment system including an electronic converter having its input connected to a system for delivering computerized sensory information coming from a remote appliance or stored in said system.

In a first application, the present invention provides a system for treating deafness.

The deafness treatment system of the invention serves to provide neural modulation of the primary auditory cortex of the brain of a patient suffering deafness by emitting ultrasound waves, preferably focused ultrasound waves, onto a specific zone of said primary auditory cortex that is of area or volume that is small, e.g. an area or a volume corresponding respectively to 1 square millimeter ($mm^2$) or to 1 cubic millimeter ($mm^3$) of the primary auditory cortex on its surface or at depth, in order to activate in highly selective manner the cortex in contact with or remote from the system, while also not interfering with the somatotopy of the brain or the language areas on the surface that are associated with the primary auditory cortex.

The ultrasound waves transmitted to the brain are waves constituting images of ambient sounds in the patient's environment that are picked up by a microphone that may be positioned towards the outside of the implant support through its top wall and the patient's skin, or that may be remote from the support in the outer ear of the patient or in any other zone and connected by wire or wirelessly to the ultrasound stimulation device in the support.

Naturally, the sensitivity with which ambient sounds are detected and their conversion into ultrasound form must be adapted to each patient as a function of the patient's degree of deafness.

A second aspect of the invention also relates to a method of treating deafness, which method consists essentially in using focused ultrasound waves emitted into the brain of a patient in order to stimulate a determined zone of the primary auditory cortex of the patient's brain.

In this method, the emitted ultrasound waves are preferably at a frequency lying in the frequency range 200 kilohertz (kHz) to 10 megahertz (MHz), and the waves are more preferably in a pulsed mode.

Furthermore, in preferred manner, the ultrasound waves are focused on a surface or a volume of the primary auditory cortex of the patient's brain respectively presenting an area of at least 1 $mm^2$ or at least 1 $mm^3$. This focusing may be performed in particular in dynamic manner with electronic means for scanning one or more different zones of the auditory cortex that is to be treated, simultaneously or consecutively by means of the emitted ultrasound waves.

Furthermore, in order to adjust the power of the transmitted ultrasound waves and in order to prevent any epileptic event, it is advantageous to monitor the electrical activity of the brain continuously in the target zone of the cortex for ultrasound emission.

This method may be performed more particularly with the help of a deafness treatment system as described above after the support has been implanted in a burr hole previously formed in the patient's cranium in register with the zone of the primary auditory cortex of the brain that is to be treated.

In another application, the present invention provides a system for treating the visual acuity of a patient.

In this application, the treatment system includes in combination one or more of the following additional characteristics:

the sensor is an image acquisition system and the ultrasound transducer focuses the ultrasound waves towards a determined zone of the patient's visual cerebral cortex; and the ultrasound stimulation device has two implantable units in which the ultrasound transducers are mounted, each implantable unit presenting an internal face through which the focused ultrasound waves are emitted, each implantable unit being provided with a concave semi-rigid flap presenting an internal face extending the internal face of the unit and through which the focused ultrasound waves are also emitted.

BRIEF DESCRIPTION OF THE DRAWINGS

Various other characteristics appear from the following description with reference to the accompanying drawings that show embodiments of the invention as non-limiting examples.

In the accompanying figures:

FIG. 3 is a diagrammatic longitudinal section of a first embodiment of deafness treatment system in accordance with the invention;

FIG. 4 is a diagrammatic longitudinal section of a second embodiment of a deafness treatment system in accordance with the invention;

FIGS. 5A and 5B show two respective variant embodiments of the bottom surface of the implantable unit of the treatment system of the invention;

FIGS. 6A and 6B show two respective variant embodiments of the top surface of the implantable unit of the treatment system of the invention;

DETAILED DESCRIPTION OF THE INVENTION

Figure 1:
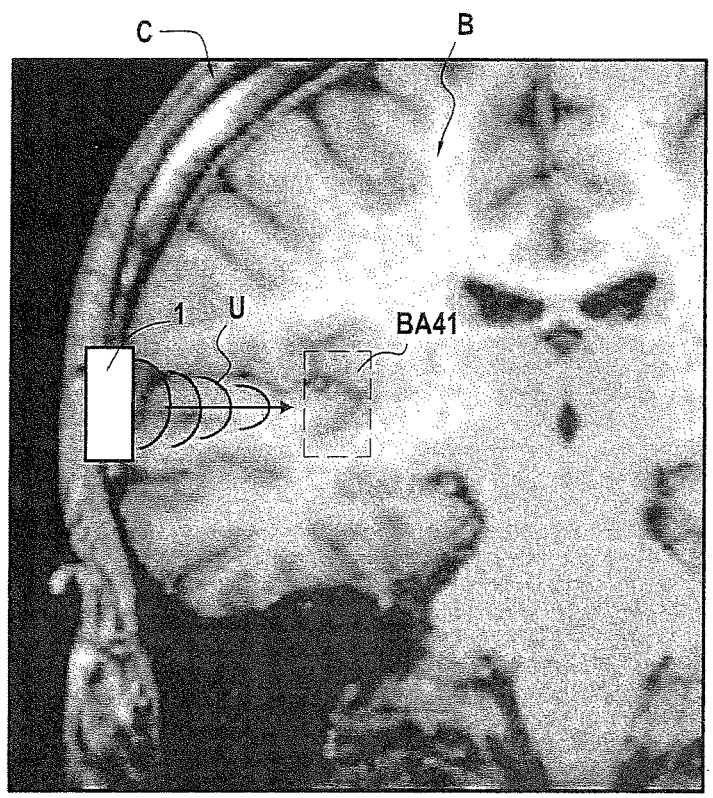
FIG. 1 is a fragmentary section of the brain in a magnetic resonance image showing the brain zone of Heschl's gyrus forming the primary auditory cortex, and the principle of activating this brain zone with the help of a system of the invention.

The present invention proposes a novel approach for treating the sensory capacities of patients. FIG. 1 to GB relate to an application of the invention in which the sensory capacity treated is hearing and in particular deafness in patients suffering from sensorineural and/or transmissive deafness. As shown diagrammatically in FIGS. 1 and 2, this new approach consists in ultrasound stimulation of the primary auditory cortex of the brain B of a patient by means of a treatment system 1 that is implantable subcutaneously in the patient's skull C and comprising an ultrasound stimulation device 3 suitable for emitting ultrasound waves U that are focused on the zone of Heschl's gyrus (BA41) and/or of the planum temporale (BA42) that form the primary auditory cortex of the human brain B. The ultrasound waves U that are emitted are pulsed waves, modulated by an electronic converter of the ultrasound stimulation device 3 as a function of a sensory signal, and more precisely of external sounds S, for example, that are sensed by at least one sensor such as a microphone 6 connected to said ultrasound stimulation device 3.

Figure 2:
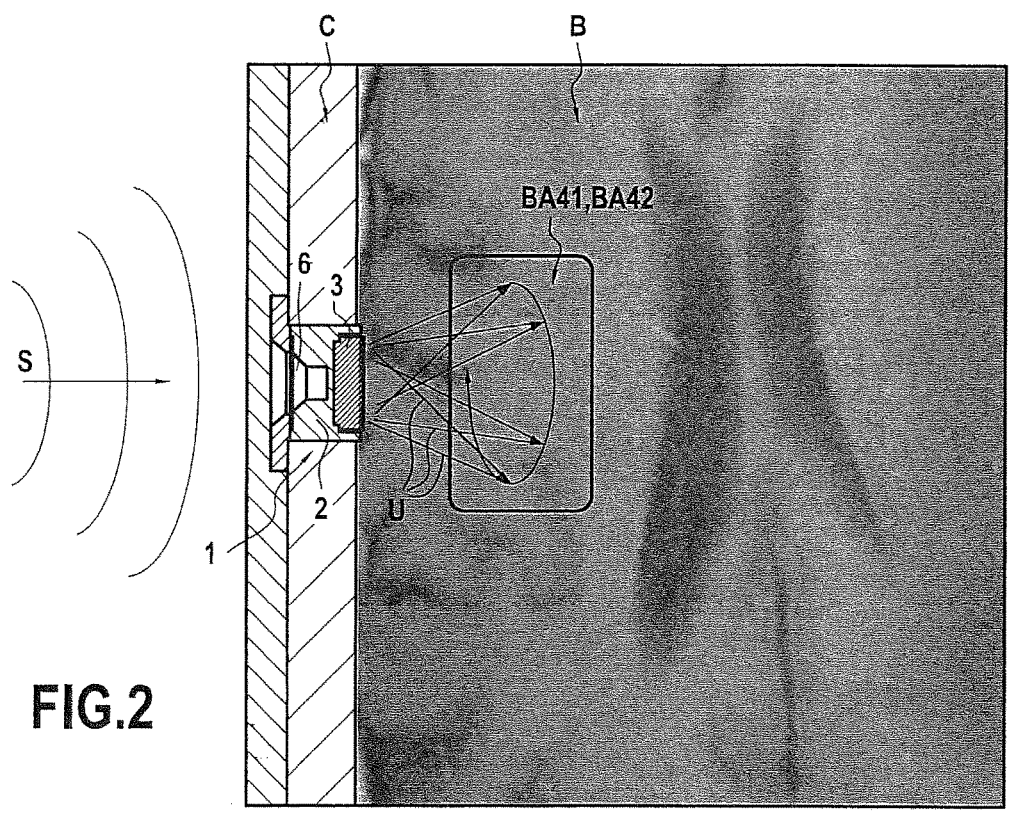
FIG. 2 is a diagrammatic section of the deafness treatment system of the invention implanted in a patient's skull in order to stimulate the primary auditory cortex of the patient's brain in accordance with the treatment method of the invention.

As shown in FIGS. 2 to 4, the deafness treatment system 1 of the invention comprises a support such as unit 2 for implanting in a patient's skull C, in particular in a burr hole made in register with the zone of the brain B that forms the primary auditory cortex. This unit 2 may be of any shape, and in particular it may be circular or rectangular in section. Advantageously, the unit 2 is made of a non-ferromagnetic material so as to ensure that it is compatible with magnetic resonance imaging (MRI). It comprises a top or external wall 21 and a bottom or internal wall 22 which are connected together by a peripheral wall 23, and it also comprises fastener means 24 for fastening the housing 2 to the patient's skull. The fastener means 24 may comprise fastener tabs 25 projecting from the sides of the top wall 21 of the unit 2 and through which screws are inserted as shown in FIGS. 6A and 6B, or they may be screw threads on the outside surface of the peripheral wall 23 to allow the unit 2 to be screwed into the burr hole in the skull. When fixed in position, the unit 2 passes right through the skull C so that its bottom wall 22 leads directly onto the brain B, as shown in FIGS. 3 and 4.

An ultrasound stimulation device 3 is arranged inside the unit 2. This ultrasound stimulation device 3 comprises at least one ultrasound transducer 4, and preferably a plurality of them, mounted and oriented in the unit 2 to emit pulsed ultrasound waves 5 through the bottom wall 22 of the unit 2 in order to generate neural depolarization and thus brain activity in the primary auditory cortex as a function of ambient sound S picked up by the microphone(s) 6. As explained above, the ultrasound stimulation device 3 includes means for emitting focused ultrasound waves U through the bottom wall 22 of the unit 2 without passing through the skull C and towards a determined zone of the primary auditory cortex of the patient's brain. The bottom wall 22 is thus made of a material that is permeable to ultrasound waves.

As shown in FIG. 5A, the bottom wall 22 of the unit 2 is preferably made up completely or at least in part of ultrasound micro-transducers 4 covering at least 50% of the area of said bottom wall 22 of the unit 2.

In one embodiment of the invention, the bottom wall 22 of the unit 2 may have an outer surface that is covered in a flexible material of varying thickness in order to procure a continuous contact interface with the brain or the dura mater in the patient's skull C and thus facilitate the propagation of ultrasound waves U into the brain B. The bottom wall 22 of the unit 2 is made of a biocompatible material, given that it is implanted inside the skull C.

In the invention, the ultrasound transducers 4 may be selected from piezo-composite elements, piezo-ceramic elements, capacitive micro-machined ultrasonic transducers (CMUTs), polyvinylidene fluoride (PVDF) elements, or other elements suitable for emitting pulsed ultrasound waves.

The ultrasound waves U emitted by the transducers arranged in the unit are pulsed ultrasound waves that are focused towards the primary auditory cortex (zones BA41, BA42) of the brain for specifically and selectively modulating the activity of the brain over a zone of very small area. The focused ultrasound waves U thus reach this zone of the brain B directly without passing through the skull C, insofar as the bottom wall 22 of the unit 2 through which the ultrasound waves pass is in contact with the brain B. The ultrasound waves emitted by the device of the invention are preferably at a frequency of the order of 200 kHz to 10 MHz.

This frequency range is particularly suitable and necessary for adapting the emission and treatment parameters of the system 1 of the invention to any patient and to any anatomical configuration, and in particular for enabling the ultrasound beam to be correctly oriented and for enabling the beam to be focused during treatment by varying the phase differences between the emitters, by adding filters, by adding acoustic lenses, or by a combination of these means.

In the example shown in the drawings, the ultrasound stimulation device 3 is placed inside a support that is in the form of a unit 2 provided with fastener means 25 for fastening to the patient's skull. It should be observed that it is possible to envisage placing the ultrasound stimulation device 3 inside a support made in the form of a membrane that is inserted inside a skull C and that includes an internal face through which the ultrasound waves are emitted and that comes into contact with the brain or the dura mater.

The ultrasound stimulation device 3 also has at least one microphone 6 adapted to pick up audible ambient sounds in the direct environment of the implanted patient. The microphone 6 in a preferred first embodiment may be positioned in the top wall 21 of the unit 2 as shown in FIG. 6A. Where appropriate, and as shown in FIG. 6B, a plurality of microphones 6 may be used so that each microphone 6 picks up a determined range of sound wavelengths.

With a single microphone 6, it is also possible to envisage separating the microphone 6 from the unit 2, in particular in order to position it in the pinna of the patient's ear and to transmit information by wire or wirelessly to the unit 2 implanted in the patient's skull C. It is also possible in the same manner to use two microphones 6, each implanted in a respective one of the patient's pinnas in order to pick up ambient sounds S in stereo.

The microphone(s) 6 is/are connected inside the unit 2 to an electronic converter 7 for decoding the sensed sounds S into electronic signals for controlling the ultrasound transducers 4. By means of the converter, the ultrasound waves U emitted by the ultrasound transducers 4 thus form ultrasound signals that are images of the sounds S sensed by the microphone(s) 6.

From the above description, it can be seen that the electronic converter 7 has its input connected to the microphone 6 in order to convert the sounds picked up by the microphone 6 into control signals for the ultrasound transducers 4. Naturally, the electronic converter 7 may serve to convert sounds that have not been picked up by a microphone, but that are generated by a simulation system incorporated in or remote from the stimulation device 3. In this embodiment, the input of the electronic converter 7 is connected to the simulation system in order to convert the simulated sound signals into control signals for the ultrasound transducers 4.

In an embodiment, the auditory information may come directly from computer data taken from computer files without it being necessary to have an auditory detection system (microphone). This makes it possible in a manner that is real to the brain to deliver computerized sensory information that is entirely virtual. Said computer files may be stored in a mobile telephone or they may be received directly from the internet in real time by such a mobile telephone. The input of the electronic converter 7 is thus connected to a system for delivering computerized sensory information coming form a remote appliance or stored in said system.

The electronic converter 7 may advantageously be made in the form of an integrated circuit and/or an electronic card including at least one microprocessor and components for converting signals from the microphone(s) 6 into signals for driving the ultrasound transducers 4. Under such circumstances, the electronic card provides intelligence for controlling the treatment system and may also host any other adjustment or control function for the treatment system 1 and its components.

In particular, the treatment system 1 of the invention also includes control means for controlling the ultrasound stimulation device 3. These control and adjustment means may be provided on the above-mentioned electronic card and may comprise means for wired or wireless communication with an external control device such as a remote control interacting with the ultrasound stimulation device in order to enable the microphone(s) 6, the converter, and the transducers 4 to be switched on and off. The adjustment and control means may also include an external control device, e.g. a monitor, suitable for connection to the ultrasound stimulation device 3 through the skin P over the skull C via a transdermal connector placed in the top wall 21 of the unit 2.

It is also possible to envisage controlling and adjusting the treatment system 1 by means of a mobile telephone and a computer application stored therein in a read-only memory (ROM) and serving to adjust and control the treatment system wirelessly, e.g. using the communications protocols defined by the IEEE 802.11 group (ISO/IEC 8802-11) and better known under the contraction "WiFi", or by the IEEE 802.15 group, also better known under the name "Bluetooth".

Finally, the deafness treatment system 1 of the invention includes power supply means 8 for electrically powering the ultrasound stimulation device, the microphones, the ultrasound transducers 4, and the control means of the device. In conventional manner, these power supply means 8 may consist in rechargeable batteries arranged in the unit 2 or indeed a subcutaneous battery implanted under the skin over the skull, or indeed away from the patient's head, e.g. under the patient's skin in the chest area, as is common practice in heart surgery for implanting pacemakers. Where appropriate, such a battery can then be charged by an external charger system, such as a magnetic system.

As shown in FIG. 6B, it is also possible to make provision for an emergency stop switch 9 to be located directly in the top wall 21 of the unit 2 level with the surface of the patient's skull.

The treatment system 1 of the invention is preferably compatible with performing analyses by magnetic resonance imaging. That is why the unit 2, and also all of the ultrasound transducers 4, the microphone(s) 6, the converter, and the other control and power supply means are preferably made of materials that are not ferromagnetic.

In a preferred embodiment of the treatment system 1 of the invention, it includes means for focusing and steering the emitted ultrasound waves U towards the target zone of the primary auditory cortex. By way of example, they may be the result of dynamic focusing or "beam steering" achieved by varying phase differences between emitters, by adding filters, by adding capacitors, by adding lenses, or by a combination of these means.

By way of example, this may be the result of a special shape for the emission faces of the ultrasound transducers 4, in particular giving these emission faces a particular concave shape, or giving such a shape to the bottom wall 22 of the unit 2 carrying the ultrasound transducers 4.

These variable focusing and steering means for the ultrasound waves U may also include means for electronically scanning one or more zones of the auditory cortex of the patient's brain B by the ultrasound waves U emitted by the ultrasound transducers.

In another embodiment of the treatment system 1 of the invention as shown in FIG. 4, the treatment system 1 may include at least one additional ultrasound emitter 10 placed in the thickness of the unit 2 in order to induce and transmit bone vibration in the skull. Such an additional ultrasound emitter 10, e.g. pressed against the peripheral wall 23 of the unit 2 as shown in FIG. 4 may be found to be particularly useful in cases of transmissive deafness that may be pure or mixed with sensorineural deafness. In this embodiment, the additional ultrasound element 10 is likewise driven by the electronic converter in the unit 2.

In another embodiment shown in FIG. 5B, the treatment system 1 may also include contact electrodes 11 in the bottom wall 22 of the unit 2, e.g. on either side of the ultrasound transducers 4, or even within the ultrasound emitters, in order to monitor the electrical activity of the brain and prevent any epileptic event.

Under such circumstances, the electrical signal from the cortex is monitored by means of electrodes 11 connected to an electronic monitoring card inside the unit 2, and preferably incorporated in or associated with the converter in order to enable the treatment system 1 to be driven in intelligent manner. In the event of an abnormal epileptogenic signal, the ultrasound emission parameters may be stopped automatically for reasons of safety or they may be modified in order to emit an inhibiting ultrasound signal.

The deafness treatment system 1 of the invention thus makes it possible to perform direct stimulation and neuromodulation of the brain activity of the primary auditory cortex of the brain B of a patient suffering from deafness by emitting ultrasound waves U that are focused and pulsed onto a very localized surface having an area of about 1 $mm^2$ of the primary auditory cortex of the patient's brain B. Such modulation of the primary auditory cortex results from transmitting ultrasound waves U that are images of ambient sounds S sensed by the microphones 6 of the treatment system 1 and they thus make it possible to provide significant treatment for sensorineural deafness pathologies in patients suffering therefrom.

The treatment system 1 of the invention also makes it possible during treatment to monitor the brain B activity of the treated patient by means of contact electrodes 11 and thus to adjust the power of the transmitted ultrasound waves U and prevent any epileptic event. The electrical activity of the brain is thus advantageously monitored continuously in the target zone of the cortex for ultrasound emission.

The treatment system 1 of the invention also makes it possible to monitor the diffusion of ultrasound waves in the brain B of the treated patient before and during treatment by recording reflected ultrasound waves returned by the brain so as to determine the acoustic attenuation index of the patient's brain, in order to detect modifications, if any, to tissue structure, and in order to detect modifications, if any, in perfusion of the brain so as to modulate and adjust the intensity of the emitted waves as well as possible.

The deafness treatment system of the invention provides a novel solution for treating deafness while not interfering with the somatotopy of the brains of patients, thus avoiding the drawback of presently-known treatment implants and procuring greater flexibility and accuracy of treatment without acting on the defective natural auditory apparatus of the patient.

It should also be observed that a treatment system analogous to that of the invention may be envisaged for stimulating the visual cortex of the brain. Under such circumstances, the structure of the treatment system then differs from that to the system of the invention essentially in that the microphones are replaced by at least one image acquisition device, e.g. a micro-camera, that is connected to the control device in which the internal converter converts the image signal coming from the acquisition device into a signal for modulating and controlling ultrasound emitters that focus their waves onto the visual cortex of the brain.

Figure 8:
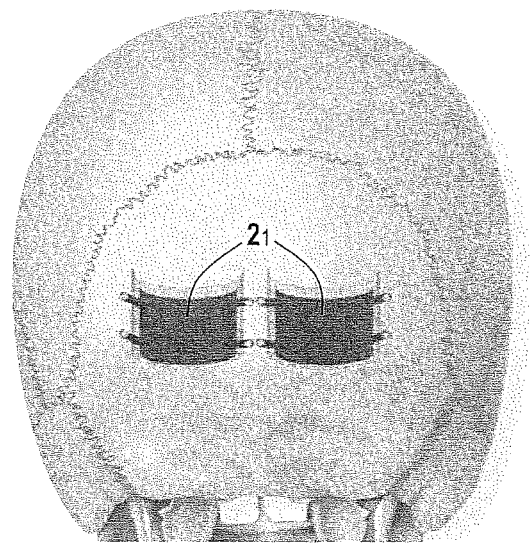
FIG. 8 is a diagrammatic posterior view of a patient's skull fitted with a vision treatment system in accordance with the invention.
Figure 9:
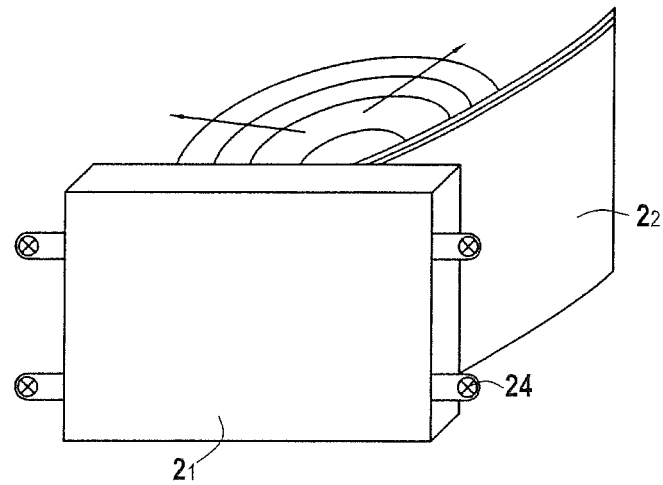
FIGS. 9 and 10 are respectively an outside view and an inside view of an embodiment of a vision treatment system in accordance with the invention.
Figure 10:
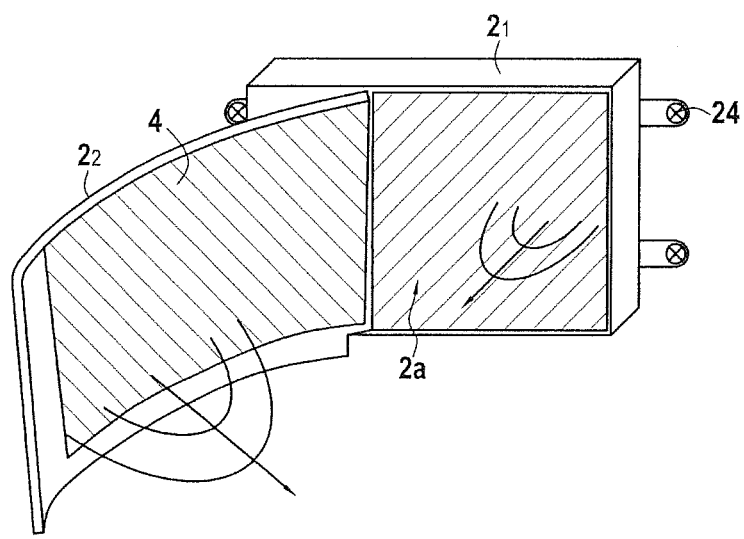

FIGS. 8 to 10 show this other preferred application of the invention to treating vision as the sensory capacity of a patient. In this application, the ultrasound stimulation device 3 has all of the technical characteristics described for the application to treating deafness, but applies to treating vision.

Figure 7:
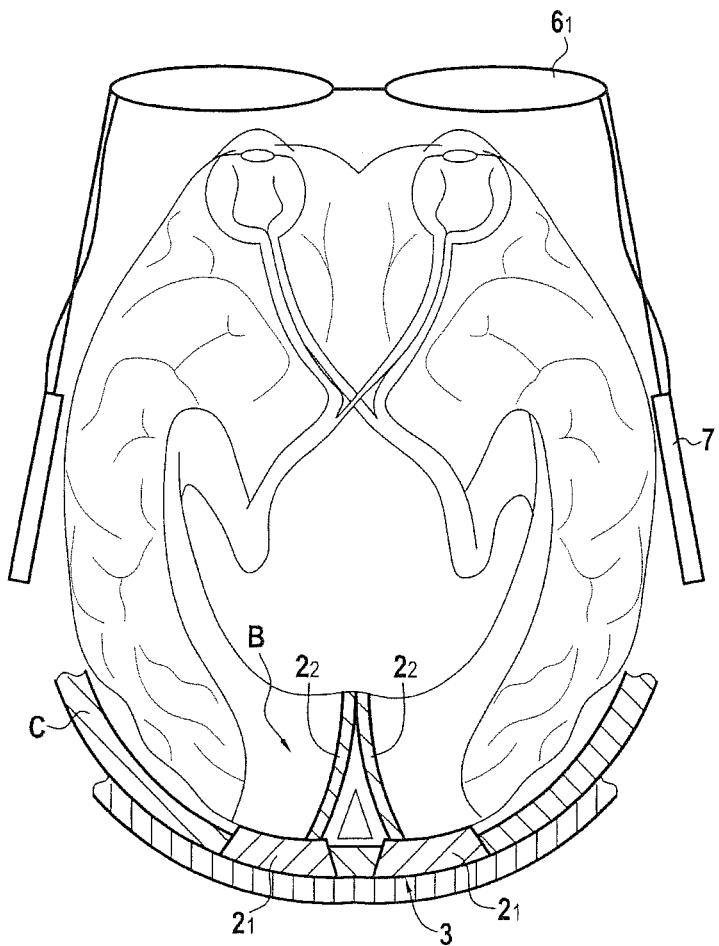
FIG. 7 is a diagrammatic section view of a vision treatment system in accordance with the invention implanted in the skull of a patient to stimulate the patient's visual cerebral cortex.

In this application, the ultrasound stimulation device 3 has two implantable units $2_1$ in which the ultrasound transducers 4 are mounted. Each implantable unit $2_1$ is provided with a semi-rigid flap $2_2$ of concave shape suitable for stimulating the median visual cerebral cortex as can be seen in FIG. 7. The unit $2_1$ and the semi-rigid flap $2_2$ present an internal face 2a through which the focused ultrasound waves are emitted as generated by ultrasound transducers 4 mounted in the unit $2_1$ and in the semi-rigid flap $2_2$. Such a unit $2_1$ is implanted in a craniectomy hole previously formed in the patient's cranium in register with the zone of the primary visual cortex of the brain that is to be treated. The semi-rigid flap $2_2$ is slid between the hemispheres after the dura mater has been opened. The unit $2_1$ is fitted with fastener means 24 for fastening to the patient's skull.

As explained with reference to FIGS. 1 to 6b, the ultrasound transducers 4 are distributed over the internal faces 2a of the implantable units in order to emit ultrasound waves that are preferably focused and at a frequency lying in the range 200 kHz to 10 MHz. The ultrasound waves are focused on a specific zone of small area of the primary visual cortex, e.g. an area of the primary visual cortex equal to about 1 mm$^2$, in order to activate the visual cortex in highly selective manner while not interfering with the somatotopy of the brain. As explained above, ultrasound waves may be focused dynamically by electronic means for scanning one or more different zones of the visual cortex that is to be treated either simultaneously or consecutively with the emitted ultrasound waves.

Furthermore, in order to adjust the power of the transmitted ultrasound waves and prevent any epileptic event, provision is made to monitor the activity of the brain continuously in the target zone of the visual cortex for ultrasound emission.

The ultrasound transducers 4 are driven as explained above by the electronic converter 7 so that the focused ultrasound signals U are an image of a sensory signal, specifically a visual signal in this application. Such a visual signal is either picked up by a sensor $6_1$, such as an image acquisition system, or else it is generated by a computer system for delivering sensory information that is entirely virtual. In the example shown in FIG. 7, the image acquisition system $6_1$ has at least one camera for taking images in the environment of the patient. The camera is connected to the input of the electronic converter 7 that is suitable for decoding and processing the visual information sensed by the camera and for transforming it into control signals for controlling the ultrasound transducers 4.

In an embodiment, the visual information may come directly from computer data coming from computer files without any need for a visual detector system (camera). This makes it possible in a manner that is real to the brain to deliver computerized sensory information that is entirely virtual. Said computer files may be stored in a mobile telephone or they may be received directly from the internet in real time by the mobile telephone. The electronic converter 7 thus has its input connected to a system for delivering computerized sensory information coming from a remote appliance or stored in said system.

In a variant embodiment, the electronic converter 7 has means for wired or wireless communication with the ultrasound stimulation device 3, and in particular with the two implantable units $2_1$. For example, the camera $6_1$ may be incorporated in eyeglasses L that also carry the electronic converter 7.

The treatment system 1 of the invention also includes means for controlling the ultrasound stimulation device 3 enabling the ultrasound stimulation device 3 to be switched on and off. As mentioned above, these control means may be implemented in various ways, e.g. with the help of an external control system connected to the ultrasound stimulation device 3 through the skin of the skull C or with the help of wireless transmission.

Naturally, the vision treatment system 1 includes power supply means 8 for electrically powering the ultrasound stimulation device 3, the camera, and the electronic converter 7. In conventional manner, these power supply means 8 may consist in rechargeable batteries arranged in the units 2 or indeed they may consist in a subcutaneous battery implanted under the skin of the skull or away from the patient's head. Such a battery may also be charged by means of an external charger system such as a magnetic system.

The treatment system 1 of the invention also makes it possible, during treatment, to monitor the cerebral activity of the brain B of the patient being treated by using contact electrodes 11 and thus to adjust the power of the transmitted ultrasound waves U so as to prevent any epileptic event. The electrical activity of the brain is thus advantageously monitored continuously in the target zone of the cortex for ultrasound emission.

The treatment system 1 of the invention also makes it possible to monitor the diffusion of ultrasound waves in the brain B of the treated patient before and during treatment by recording reflective ultrasound waves as returned by the brain in order to determine the acoustic attenuation index of the patient's brain, in order to detect modifications, if any, to tissue structure, and in order to detect modifications, if any, in perfusion of the brain so as to modulate and adjust the intensity of the emitted waves as well as possible.

The invention claimed is:

1. A system for treating at least one sensory capacity of a person with a help of a stimulation device comprising an electronic converter for converting a sensory signal into an electronic signal for controlling at least one transducer for emitting signals that are images of the sensory signal, the system being characterized in that the stimulation device is a device for direct ultrasound stimulation of a sensory cortex of a patient's brain, the ultrasound stimulation device comprising:
- at least one support that is adapted to be implanted in a patient's skull and that includes at least one internal wall; and
- at least one ultrasound transducer carried by the support (2) and adapted for emitting ultrasound waves (U) through the internal wall of the support towards a determined zone of the sensory cortex of the patient's brain in order to generate modulation of a brain activity in the cortex, the ultrasound transducer being driven by the electronic converter to emit ultrasound signals that are images of the sensory signal;
- wherein the ultrasound stimulation device is provided with a flap presenting an internal face through which ultrasound waves are emitted, wherein the flap is designed to be slid between hemispheres of the patient's brain;
- wherein the flap is concave and semi-rigid and the implanted support comprises an internal face through which ultrasound waves are emitted, and the flap has ultrasound waves also emitted therethrough.

2. A treatment system according to claim 1, characterized in that the electronic converter has its input connected to at least one sensor adapted to pick up a sensory signal present in an environment of the person.

3. A treatment system according to claim 1, characterized in that the support comprises a fastener for fastening to the patient's skull and the support having an external wall (21) connected to the internal wall via a peripheral wall.

4. A treatment system according to claim 2, characterized in that the sensor is an image acquisition system and in that the ultrasound transducer focuses the ultrasound waves towards a determined zone of a patient's visual cerebral cortex.

5. A treatment system according to claim 1, characterized in that the internal wall of the support includes an external surface covered in a flexible material of varying thickness to provide a continuous contact interface with the brain or a dura mater and to facilitate propagation of ultrasound waves into the brain.

6. A treatment system according to claim 1, comprising an external remote control for controlling and driving the ultrasound stimulation device wirelessly.

7. A treatment system (1) according to claim 1, comprising an external control device connectable to the ultrasound stimulation device (3).

8. A treatment system according to claim 1 comprising at least one rechargeable battery arranged in the support or implanted under a skin of the patient's body.

9. A treatment system according to claim 1, comprising electrodes on an external contact surface of the internal wall of the support for monitoring an electrical activity of the brain and for preventing any epileptic event.

10. A treatment system according to claim 1, comprising an emergency stop switch in a top wall of the support.

11. A treatment system according to claim 1, wherein the electronic converter has an input thereof connected to a system for delivering computerized sensory information that is stored in said system or that comes from a remote appliance.

12. A method of treatment comprising using ultrasound waves emitted in a cranium of a patient in order to stimulate a determined zone of a sensory cortex of a patient's brain using a treatment system, wherein the method further comprises:
- forming a craniectomy hole in the patient's cranium in register with a zone of a primary visual cortex of the brain;
- opening dura mater;
- sliding a flap of an ultrasound stimulation device between the brain hemispheres; and
- emitting ultrasound waves through an internal face of the flap; wherein the treatment system comprises:
- an electronic converter for converting a sensory signal into an electronic signal for controlling at least one transducer for emitting signals that are images of the sensory signal, the treatment system being characterized in that the ultrasound stimulation device is a device for direct ultrasound stimulation of the sensory cortex of the patient's brain, the ultrasound stimulation device comprising:
- at least one support that is adapted to be implanted in the patient's skull and that includes at least one internal wall; and
- at least one ultrasound transducer carried by the support and adapted for emitting ultrasound waves through the internal wall of the support towards the determined zone of the sensory cortex of the patient's brain in order to generate modulation of a brain activity in the cortex, the ultrasound transducer being driven by the electronic converter to emit ultrasound signals that are images of the sensory signal; wherein the ultrasound stimulation device is provided with the flap presenting an internal face through which ultrasound waves are emitted, wherein the flap is designed to be slid between hemispheres of the patient's brain and is used after the support has been mounted in the patient's skull in register with the zone for treatment of the sensory cortex of the brain;
- wherein the flap is concave and semi-rigid and the implanted support comprises an internal face through which ultrasound waves are emitted, and the flap has ultrasound waves also emitted therethrough.

13. A method of treatment according to claim 12, characterized in that a frequency of the emitted ultrasound waves lies in a frequency range 200 kHz to 10 MHz, approximately.

14. A method of treatment according to claim 12, characterized in that an electrical activity of the brain is monitored continuously in the target zone of the cortex for ultrasound emission in order to adjust the power of the transmitted ultrasound waves and to prevent any epileptic event.

15. A method of treatment according to claim 12, comprising recording reflected ultrasound waves returned by the brain so as to determine the acoustic attenuation index of the brain.

16. The treatment system according to claim 1, wherein the flap has a concave shape suitable for stimulating the median visual cerebral cortex.

17. The treatment system according to claim 1, wherein the flap has ultrasound transducers mounted therein.

* * * * *